(12) United States Patent
Gille et al.

(10) Patent No.: US 10,667,784 B2
(45) Date of Patent: Jun. 2, 2020

(54) COMPONENT-BASED CATHETER LAB INTRAVASCULAR ULTRASOUND SYSTEM

(75) Inventors: Henrick K Gille, Oceanside, CA (US); Vincent Burgess, San Diego, CA (US); Nancy Perry Pool, El Dorado Hills, CA (US); Edward A Oliver, Folsom, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 820 days.

(21) Appl. No.: 13/481,693

(22) Filed: May 25, 2012

(65) Prior Publication Data

US 2012/0265077 A1    Oct. 18, 2012

Related U.S. Application Data

(63) Continuation of application No. 11/549,402, filed on Oct. 13, 2006, now abandoned.
(Continued)

(51) Int. Cl.
*A61B 8/12* (2006.01)
*G01S 7/52* (2006.01)
(Continued)

(52) U.S. Cl.
CPC ............ *A61B 8/12* (2013.01); *A61B 5/02007* (2013.01); *A61B 8/461* (2013.01); *A61B 8/467* (2013.01);
(Continued)

(58) Field of Classification Search
CPC ................ A61B 8/12; A61B 8/4461
(Continued)

(56) References Cited

U.S. PATENT DOCUMENTS

| | | | |
|---|---|---|---|
| 5,229,933 | A | 7/1993 | Larson, III |
| 5,243,989 | A | 9/1993 | Saiga et al. |

(Continued)

FOREIGN PATENT DOCUMENTS

| | | |
|---|---|---|
| GB | 345543 | 3/1931 |
| JP | 3-181877 A | 8/1991 |

(Continued)

OTHER PUBLICATIONS

European Patent Office International Search Report, for EP Application No. 06825927.4, dated Jun. 28, 2010, 10 pages.
(Continued)

*Primary Examiner* — Hien N Nguyen (57) ABSTRACT

A componentized intravascular ultrasound system is disclosed that flexibly integrates with a catheter lab infrastructure for acquisition and display of intravascular information in a catheter lab environment. The system includes a patient interface module (PIM) adapted to hold a catheter having an imaging probe located near a distal end, a control panel, a monitor for displaying images and patient data, and a processing unit. The processing unit is communicatively coupled to the PIM, the control panel, and the monitor. Furthermore the processing unit adapted to: coordinate operation of the PIM, the control panel, and the monitor; and generate images from image data provides by the PIM. The PIM, control panel and monitor are independently positionable with regard to one another.

26 Claims, 6 Drawing Sheets

Related U.S. Application Data (60) Provisional application No. 60/727,146, filed on Oct. 13, 2005, provisional application No. 60/825,813, filed on Sep. 15, 2006.

(51) Int. Cl.
  *A61B 5/02* (2006.01)
  *G01S 15/89* (2006.01)
  *A61B 8/00* (2006.01)
  *A61B 6/00* (2006.01)
  *A61B 5/055* (2006.01)

(52) U.S. Cl.
  CPC .............. *A61B 8/468* (2013.01); *A61B 8/565* (2013.01); *G01S 7/5208* (2013.01); *G01S 7/52084* (2013.01); *G01S 15/899* (2013.01); *A61B 5/055* (2013.01); *A61B 6/4441* (2013.01); *A61B 8/4411* (2013.01); *A61B 8/464* (2013.01)

(58) Field of Classification Search
  USPC ........................................................ 600/462
  See application file for complete search history.

(56) References Cited

U.S. PATENT DOCUMENTS

| | | | | |
|---|---|---|---|---|
| 5,765,565 | A | * | 6/1998 | Adair .............................. 128/849 |
| 6,148,095 | A | | 11/2000 | Prause et al. |
| 6,361,497 | B1 | * | 3/2002 | Lathbury et al. .............. 600/437 |
| 6,673,015 | B1 | | 1/2004 | Glover et al. |
| 6,813,512 | B2 | | 11/2004 | Aldefeld et al. |
| 6,817,947 | B2 | * | 11/2004 | Tanskanen ............... A63F 13/12 463/41 |
| 2002/0133239 | A1 | | 9/2002 | Rebellius et al. |
| 2003/0236443 | A1 | * | 12/2003 | Cespedes ................. A61B 5/01 600/29 |
| 2004/0179332 | A1 | | 9/2004 | Smith et al. |
| 2005/0014996 | A1 | * | 1/2005 | Konomura et al. .......... 600/175 |
| 2005/0059892 | A1 | | 3/2005 | Dubois et al. |
| 2006/0165040 | A1 | * | 7/2006 | Rathod ................... G06Q 10/10 370/335 |
| 2007/0016028 | A1 | * | 1/2007 | Donaldson et al. .......... 600/437 |
| 2007/0016029 | A1 | | 1/2007 | Donaldson et al. |

FOREIGN PATENT DOCUMENTS

| | | | |
|---|---|---|---|
| JP | 05-130993 | A | 5/1993 |
| JP | 09-285463 | A | 11/1997 |
| JP | H09322894 | A | 12/1997 |
| JP | 2001-299756 | A | 10/2001 |
| JP | 2001-344354 | A | 12/2001 |
| JP | 2002-085405 | A | 3/2002 |
| JP | 2002-526144 | A | 8/2002 |
| JP | 2002-534148 | A | 10/2002 |
| JP | 2005-245961 | A | 9/2005 |
| WO | WO 00/19907 | | 4/2000 |
| WO | WO 00/40156 | | 7/2000 |

OTHER PUBLICATIONS

Translation of Final Decision of Rejection received in Japanese Application No. 2008-535719, dated Jan. 14, 2014, 3 pages.
International Search Report received in Patent Cooperation Treaty Application No. PCT/US06/40127 dated Apr. 5, 2007, 1 page.
Written Opinion of the International Searching Authority received in Patent Cooperation Treaty Application No. PCT/US06/40127 dated Apr. 5, 2007, 3 pages.
Translation of Office Action received in Japanese Patent Application No. 2008-535719 dated Dec. 16, 2011, 3 pages.
European Patent Office, "European Office Action for Application No. EP 06 825 927.4," dated Nov. 10, 2015, 5 pages.
European Patent Office, "Examination Report" for Application No. 06825927.4, dated Sep. 13, 2016, 5 pages.

* cited by examiner

| C _ | P _ | S _ | M *_ | R *_ | A *_ |
|---|---|---|---|---|---|
| CPU | Primary Monitor | Secondary Monitor | Main Control Panel | Remote Control Panel | Archiving Station |
| 1 On PT, Spanning Rails | 1 On PT VoIc Monitor | 0 NR | 1 On PT, LHS orRHS | 0 NR | 0 NR |
| 2 On PT, LHS Rail | 2 Use Existing Customer Monitor | 1 In CR, VoIc Mon., on Table | 2 In CL, on Wall | 1 In CL, on Wall | 1 Customer DICOM |
| 3 On PT, RHS Rail | 3 In CR, VoIc Monitor | 2 In CL VoIc Monitor, Wall | 3* In CL, on IV cart | 2 In CL, on IV cart | 2* Archive in CR |
| 4 In ER Wall Mounted | | 3 VoIc Mon in Display Cluster | 4* In CR on Table | 3* In CR on Table | 3* Archive in 2nd CR |
| 5 In ER Table Mounted | | 4 Custom Display | 5* in CR Wall | 4* in CR Wall | |
| 6 In CR Floor Mount | | | *=H Attach Printer | *=H Attach Printer | *=H Attach Printer |
| 7 In CR Table Mounted | | | | | |

FIG. 6

COMPONENT-BASED CATHETER LAB INTRAVASCULAR ULTRASOUND SYSTEM

CROSS-REFERENCE TO RELATED APPLICATION

This application is a continuation of U.S. application Ser. No. 11/549,402 filed Oct. 13, 2006, which claims priority of Gille et al. U.S. Provisional application Ser. No. 60/727,146 filed on Oct. 13, 2005, entitled "Component-Based Catheter Lab Intravascular Ultrasound System," and Pool et al. U.S. provisional application Ser. No. 60/825,813 filed on Sep. 15, 2006, entitled "Control Panel for a Catheter Lab Intravascular Ultrasound System", each of which is expressly incorporated herein by reference in its entirety including the contents and teachings of any references contained therein.

FIELD OF THE INVENTION

The present invention generally relates to the field of ultrasound imaging systems, and more particularly to systems used to diagnose and treat vascular disease.

BACKGROUND OF THE INVENTION

The development of new medical technologies has provided an increasing number of options available to doctors for the diagnosis and treatment of cardiovascular diseases. The availability of such equipment has improved the ability of doctors and surgeons to detect and treat cardiovascular disease. Intravascular imaging technologies have enabled doctors to create and view a variety of images generated by a sensor inserter within a vasculature. Such images compliment traditional radiological imaging techniques such as angiography by providing images of the tissue within vessel walls rather than showing a two dimensional lumen image.

In the area of cardiovascular imaging, doctors now routinely rely upon a variety of products and technologies including intravascular ultrasound (IVUS), angiogram, and MRI imaging devices. In fact, a recent trend is to combine external and invasive (IVUS) imaging methods within a single session with a patient. In fact such diverse technologies are now used even simultaneously to improve tracking the progress of a diagnostic and/or treatment device mounted upon a catheter during treatment of a patient.

Known IVUS systems such as the InVision system from Volcano Corporation are relatively large multi-component systems that are mounted upon a trolley that takes up a space about the size of a small refrigerator. These systems contain the displays, control panels, power supplies and computers in a single large chassis that is mounted upon a set of wheels to facilitate easy movement to any operating room/imaging lab where it is needed.

The benefits of IVUS systems are well documented. However, in a relatively crowded operating room environment, the mechanical configuration of known trolley-based IVUS systems can pose problems with regard to having clear, unobstructed access to a patient. Therefore, recent versions of IVUS systems have expanded the form factor options from the trolley to ones that adopt a "distributed integration" approach wherein the components are separated (i.e., they no longer reside within a single chassis) and integrated with existing support structures within an operating room/catheter lab. In a known system, a monitor is mounted permanently on a boom above a patient table, a controller is mounted upon a rail on the patient table, a CPU is placed proximate the patient table, and a patient interface module is connected to the CPU via a short cable. In the known system, the short power/communications cable connecting the patient interface module to the patient interface module is limited in length and restricts placement of the CPU.

Another potential barrier to adoption of invasive imaging techniques is the ease of use of such systems. Known systems tend to include generalized interfaces that are not particularly suited/adapted for use in a catheter lab where space is limited and ease of use is desired when a procedure must be completed potentially very quickly and without error. Training is a problem due to staff turn over, so a system that is easy to learn how to use and retain the information is very important.

SUMMARY OF THE INVENTION

In accordance with the present invention an intravascular ultrasound (IVUS) system is integrated into a catheter lab/operating room as a set of modular IVUS system components. Display, processing unit and control panel components can be placed in their most desired locations (even in another room) without restrictions arising from cable length limitations.

In particular embodiments, low power processors like the new Intel Pentium Sossaman processor reduce the cooling requirements thereby potentially reducing the size of blower fans and the processing unit chassis. A reduced chassis size expands the potential locations for the processing unit (e.g., under a patient table). The display can be mounted in several locations in the catheter lab or control room. The control panel can be mounted remotely and outside a sterile field.

The system includes a control panel through which a user controls the acquisition and display of IVUS image information. In illustrative embodiments the physical interface of the control panel is divided into regions associated with particular workflow functionality. The combination of functional regions and functions performed by controls (e.g., buttons, mouse/trackball, etc.) within particular regions facilitates a superior user experience including an enhanced learning curve as well as an ability to make selections by feel (as opposed to sight). In the disclosed embodiment a first region includes a set of IVUS action keys, a second region includes pointer navigation controls (e.g., trackball) with multi-button mouse functionality, and a third region includes controls for selecting modes of IVUS operation.

BRIEF DESCRIPTION OF THE DRAWINGS

While the claims set forth the features of the present invention with particularity, the invention, together with its objects and advantages, may be best understood from the following detailed description taken in conjunction with the accompanying drawing of which:

DETAILED DESCRIPTION OF THE DRAWINGS

The IVUS (intravascular ultrasound) system embodying the present invention is based on the functionality derived from existing IVUS systems, including ChromaFlo and other features present in the existing system. An exemplary system uses legacy internal circuit board architectures incorporated into previously provided systems, including, for example, analog and digital boards. The components of an exemplary system and their general descriptions are provided herein below with reference to FIG. 1. The components are physically divided, appropriately sized, and connected in a manner that improves their ability to seamlessly integrate with existing catheter lab/operating room infrastructure and thereby maximize accessibility to a patient and other medical equipment in the room.

Figure 1:
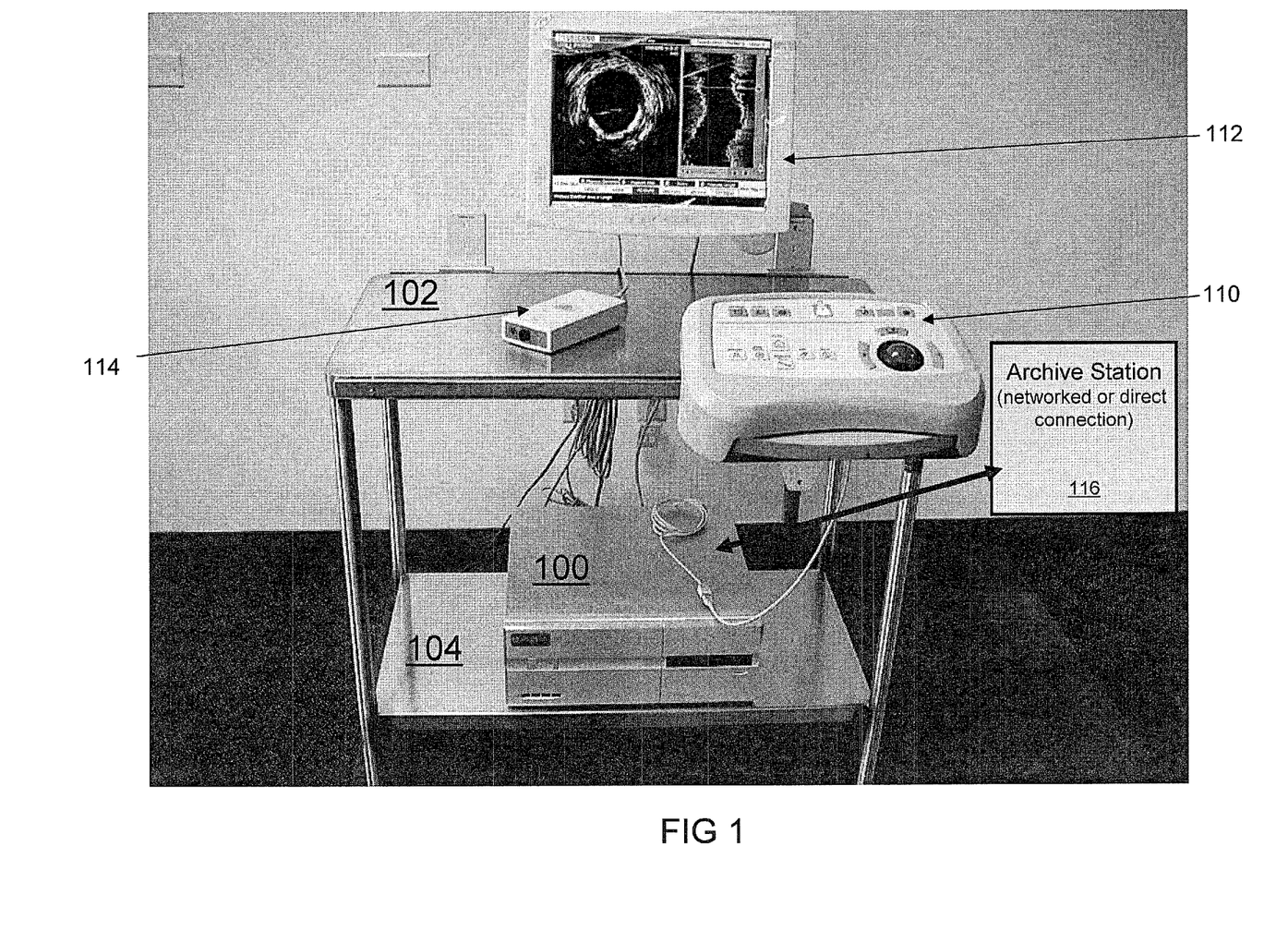
FIG. 1 is a schematic drawing depicting the components and communicative connections of an exemplary IVUS system suitable for integration with catheter lab/operating room infrastructure.

Turning to FIG. 1, a photographic image depicts a set of the primary components of an IVUS system suitable for integration in a catheter lab/operating room environment. It is noted that the exemplary installation depicted in FIG. 1 depicts mounting/placement of the various components on a "shortened" patient table 102 (used for demonstration purposes). In an actual operating room environment the table is significantly longer and more sturdy in construction to support a patient during a catheterization procedure.

A processing unit 100, incorporating many of the capabilities and functionality of known personal computers, coordinates operation of the peripheral components of the exemplary IVUS system, processes commands from attached controllers, issues control commands to an IVUS device (via a PIM) and processes IVUS data received from the IVUS device to render corresponding graphical IVUS image data. The resulting IVUS image data drives communicatively coupled graphical displays. The image data is also stored on both local and networked data storage devices.

In an exemplary embodiment, a housing for the processing unit 100 has suitable dimensions to facilitate placement of the processing unit 100 in a variety of desirable locations, both proximate (e.g., on a shelf 104) and remote from the patient table. In the illustrative example the housing of the processing unit 100 occupies a space of about 16 inches square and about 6 inches deep. The dimensions of the processing unit 100 (housing) vary in accordance with various embodiments of the invention and should not be taken as limiting the scope of the invention. Furthermore, the location of the processing unit 100 is very flexible in view of its size and the signal transmission capabilities of physical communications links between the processing unit 100 and peripherally connected components including: a control panel 110, a monitor 112, and a patient interface module (PIM) 114. The interconnect cabling and the peripheral components are described further herein below.

The processing unit 100 includes a commercially available mother board with, for example, an INTEL PENTIUM Sossaman (dual-core, low-power consumption) microprocessor, 2 GB of system RAM, one 3.5" hard drive, a medical grade power supply, an ultrasound signal processing card, and a remote control interface card. In an exemplary embodiment the external interface of the processing unit 100 and embedded control logic support multiple, simultaneously active (i.e., sending asynchronously processed control instructions to the processing unit 100) control panels (e.g., control panel 110) and multiple remote monitors (e.g., monitor 112). The multiple control panels and remote monitors are not limited to two, and can indeed exceed two. Support of multiple active controllers (e.g., control panel 110) allows two or more users to send control signals governing the operation of the system to the processing unit 100 without locking out any of the simultaneous users. Such operating mode supports remote assistance for a user operating the local control panel 110.

The control panel 110 and the monitor 112 are connected via communications cabling supporting remote positioning/operation of the peripheral components from the processing unit 110 during a catheterization procedure. By design, the processing unit 100 is compact, relatively light weight, very quiet and operates without direct user contact once powered up. The processing unit 100's housing, by way of example, incorporates mechanical mounting features (e.g., hooks, clamps, etc.) allowing the processing unit 100 to be secured to mounting rails on the patient table 102. Alternatively, the processing unit 100 is mountable on wall attached rails. In various embodiments, the processing unit 100 includes a variety of storage devices including, for example: a hard drive, DVD/CD burner/player, VCR recorder/player, etc.). The secondary storage device can also be a peripheral device attached via, for example, a USB cable to the processing unit 100.

Figure 2:
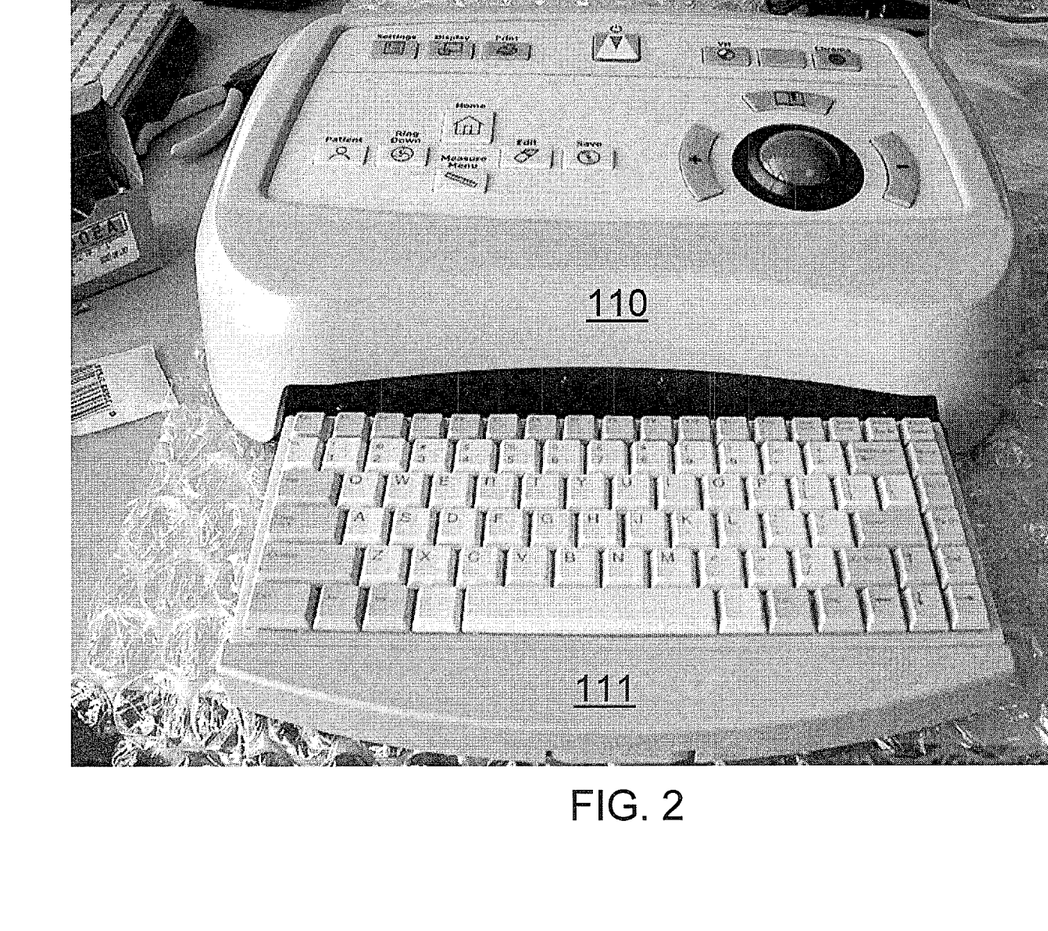
FIG. 2 depicts an exemplary control panel including a keyboard in its slideout position.

Turning to the control panel 110 component of the system, in the exemplary embodiment, the control panel 110 includes a plastic housing that holds various user input interfaces. Approximate dimensions of the control panel are: 10"×16"×4" (H×W×D). By way of example, the exemplary control panel 110 includes a slide out keyboard 111 (see, FIG. 2) and a touch interface (described further herein below with reference to FIG. 5). The enclosure is mountable on a variety of structures including, for example, a support arm attached to a rail of the patient table 102 or an articulated wall mount. The control panel 110 can be placed away from the immediate vicinity of the patient table 102 such as on a table in a remote control room or mounted to a roll around (e.g., IV pole) cart. The control panel 110 is communicatively coupled to the processing unit 100 via a cable of potentially significant length. In yet other embodiments, the control panel is located on a table near a secondary local medical grade display (not shown) which receives a copy/clone of the primary image displayed on the monitor 112. The second display (e.g., a 15 inch LCD monitor) requires an additional cable from the processing unit 100. The control panel 110 includes, by way of example, an additional USB port so that it can also be connected to a printer or other suitable USB-enabled peripheral device.

Referring now to the monitor 112, in an exemplary embodiment the monitor 112 is a 19 inch LCD monitor (e.g., an InVision monitor) for providing an image, based upon image data rendered by the processing unit 100, to viewers in the vicinity of the patient table 100. In an exemplary embodiment the monitor 112 is mounted to an articulated arm attached near the "foot" end of the patient table 102. The mounting arm incorporates many degrees of motion freedom thereby enabling rotating and positioning the monitor 112 so that it is entirely under the patient table and out of the way if desired. When needed for IVUS, the monitor 112 is repositioned so that it is easily viewed by a catheter lab technician standing near the patient table 102.

The remote control/display system supported by the processing unit 100 is used to allow remote control of the processing unit 110 by multiple remote control devices (e.g., the control panel 110). The system similarly supports remote display of video images from the processing unit 100 on multiple displays.

Primary system components on the processing unit 100 supporting communications between the processing unit 100 and a peripheral control/display device are a CPU integrated signal sender and a remote signal receiver. The interconnection is by means of a single CAT6 double shielded cable from the CPU to each of the 2 remote control panels and each of the 2 remote displays. Power is provided over the CAT6 cable so no remote power supply is required.

The exemplary system also includes a known PIM 114 to which appropriate IVUS catheters are communicatively coupled for an imaging session. The PIM 114 can be any of a wide variety of interface modules that interface imaging catheters to a processing unit such as processing unit 100.

Another notable feature of the illustrative embodiment is the ability of the components to be separated by potentially large distances. Through the use of high quality cabling (both USB and VGA) and sufficiently powered transmission interfaces (e.g., in-line buffer amplifiers), components of the system (including remote instances of peripheral control panels and monitors) are positioned outside the immediate vicinity of the patient table 100, such as across the room or even in a separate room up to 150 feet from the patient table, without significant signal loss. In an exemplary embodiment, the cable connecting the PIM 114 and the processing unit 100 is up to approximately 100 feet. In such circumstances the extended length is accommodated by a greater gauge wire in the connector cable as well as through adjustments for signal transmission delays.

In an exemplary embodiment wherein the processing unit 100 is mounted on a lower shelf of the patient table 102, the wiring to and from the processing unit 100 is routed to remotely located independently/flexibly located (remotely located) peripheral components, including possibly remotely located versions of the control panel 110 and the monitor 112, by cabling strung across the floor under suitable cable covers. Cabling for other peripheral components positioned in the proximity of the patient table 102, such as the catheter lab control panel 110 and the patient interface module (PIM) 114, are routed directly from the processing unit 100 to these components. In the illustrative example in FIG. 1, the monitor 112 is mounted to the patient table 102, in close proximity to the processing unit 100, and a direct VGA cable connection is provided. The remaining cable is CPU AC power which should be available from an AC outlet on or near the patient table mounting pedestal. There is no AC power required for the control panels attached to the CPU.

The cabling between the various components supports communications using a variety of protocols. By way of example, the control devices operate via USB and TCP/IP protocols. The video/analog cables utilize a VGA or analog Ethernet scheme. However, in alternative embodiments digital video signaling schemes are used. Finally, while cables are described for communicatively coupling the components, in alternative embodiments wireless technology links one or more of the inter-communicating components of the system.

The exemplary component-based system also includes an archive station 116. In the illustrative embodiment depicted in FIG. 1, data is moved from the processing unit 100 to a shared image data server running on the archive station 116. By way of example, the data is transmitted via Ethernet protocol to a DICOM workstation (the archive station 116) for storage within an appropriate directory or database, or alternatively burning the image data to DVD or other removable computer readable memory media. Data can also be moved from the processing unit 100 by means of a removable flash drive of, for example, 4 GB capacity. The flash drive is thereafter installed on another computer including a DVD burner for review or burning to a DVD. However, in yet another alternative arrangement, archival capabilities are provided in the form of a desk top/tower PC workstation including a commercial monitor (e.g., a 15 inch LCD) and a DVD writer. The workstation connects to the processing unit 100, for example, by means of an Ethernet. The files stored on the hard drive of the processing unit 100 are moved to the workstation for review and archiving to a DVD without impacting the operation of the processing unit 100. In still another alternative embodiment the functionality and hardware (e.g., hard drive and CD/DVD burner) of an archive station is incorporated into the processing unit 100. A printer, such as a color dye sublimation printer, is optionally attached to the workstation to permit image printing.

Figure 3:
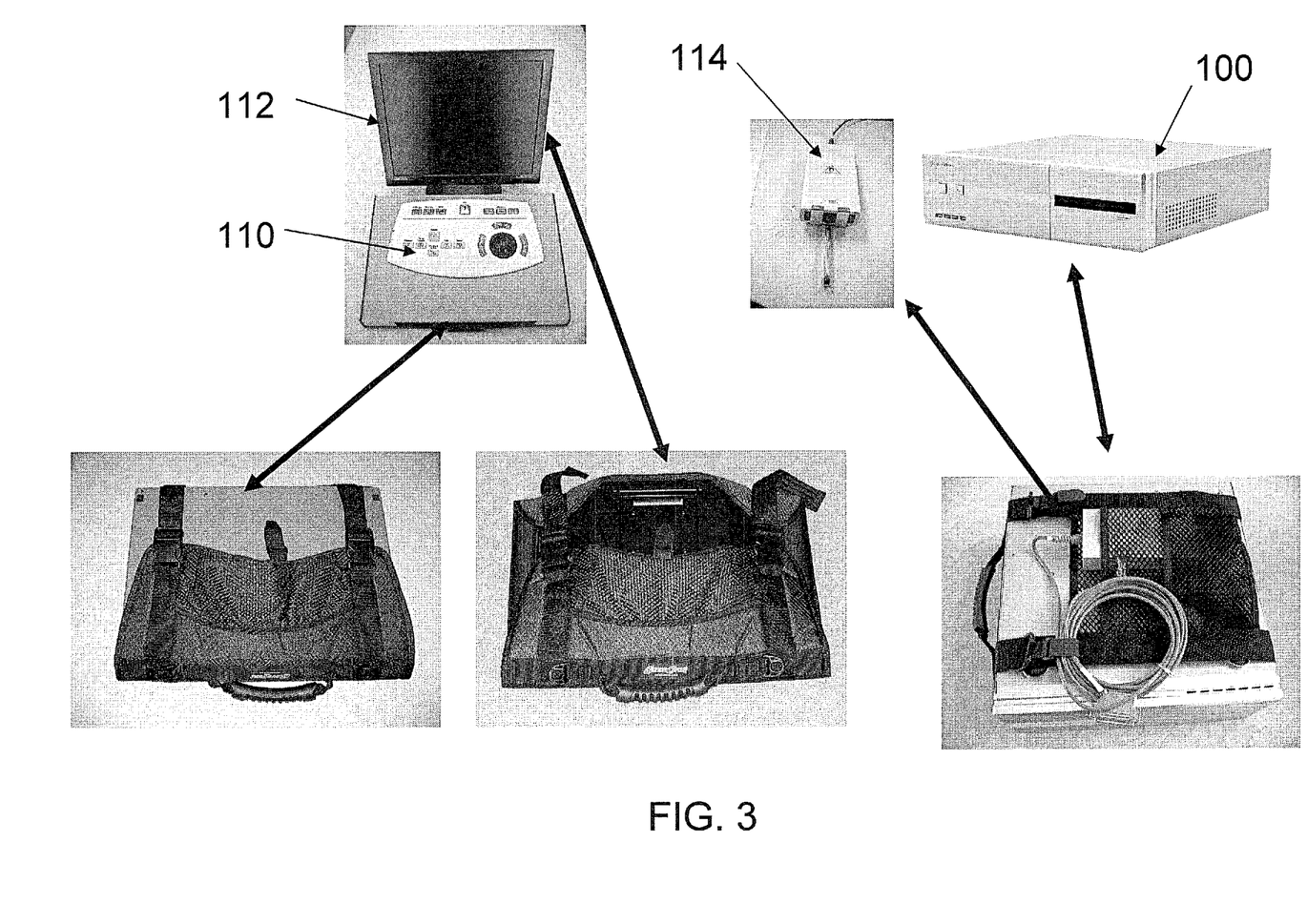
FIG. 3 depicts an exemplary portable configuration of the system including components and their associated carrying case configuration.

The componentized arrangement of the disclosed system facilitates providing a portable system. A portable version of the system (see, FIG. 3) depicted in FIG. 1 uses the same processing unit 100 depicted in FIG. 1. However, the processing unit 100 is mounted in a carrier to allow it to be easily transported. The control panel 110 and archive station 116 are transported by carriers. The monitor 112 is potentially any one of a variety of commercially available medium scale (e.g. 15 inch) LCD monitors. If desired, an optional collapsible cart, chosen from one of many commercially available models is used to transport the separately bagged/encased components.

Standard-dimensioned mounting rails are generally available in catheter labs. The installation kit for the system, by way of example, includes a set of rail mounting hardware to allow customization of the mechanical installation to meet the unique positioning requirements of each catheter lab.

Figure 4:
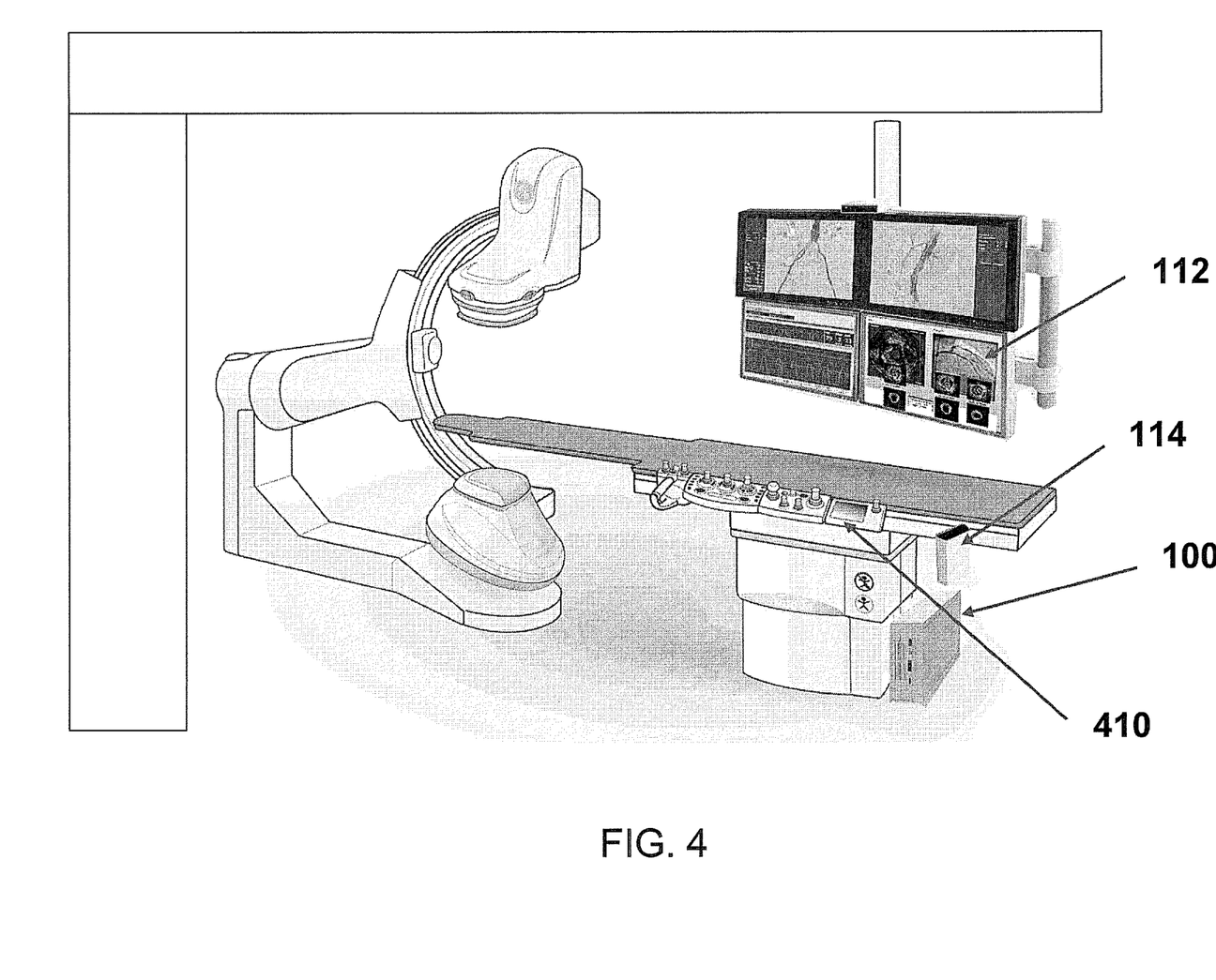
FIG. 4 depicts an exemplary integrated system including an integrated third party controller.

Another aspect of the disclosed system is interoperability support. In the exemplary embodiment, the processing unit 100 includes an Ethernet connection that allows connection of the processing unit 100 to a hospital LAN, DICOM workstation, archive workstation, or remote control consoles such as ones provided from GE (see, e.g., controller 410 in FIG. 4), Siemens or other manufacturers. In support of this functionality, one or more additional software modules are provided to interpret commands issued by these remote control devices and provide the proper response (including image data translators to match the supported protocols of the attached devices and their associated image display systems).

The following summarizes a set of functional/operational features of an exemplary componentized system described herein above. First, the system unobtrusively integrates with existing equipment in a catheter lab. As such the system can always be in position, always powered and ready to perform an IVUS imaging session. Second, the system occupies no floor space. Third, the system does not noticeably alter the lab's working environment since it generates very little noise (the low power processors generate less heat and therefore smaller fans can be used). Fourth, the system accepts, and processes control commands issued from multiple, simultaneously active distinct controllers. Multiple users can simultaneously submit control commands that are processed as they are received by the processing unit 100. Similarly, the system supports multiple, potentially remotely located, monitors for displaying IVUS images rendered by the processing unit 100. Sixth, the system can be dismantled and packaged in hand-held portable carriers in a portable embodiment. The above functionality is provided by a system that incorporates all the functional capabilities of full-size currently available IVUS systems.

While various examples are provided herein, it is noted that other embodiments include any of a variety of alterations. For example, the processing unit 100 can occupy any of a variety of form factors such as a cube. The motherboard of the processing unit 100 is, by way of example, any microATX or ATX sized board, allowing any of the commercially available PENTIUM processors to be used. The control panel 110 can be connected by means of a WiFi connection using suitable adapters. The video image from the IVUS system can be broadcast to remote locations using wireless technology. Any number of monitors, keyboards, trackballs or mice can be attached to the processing unit 100 and used simultaneously (no controller lock out) with their asynchronous requests being handled as they are received by the processing unit 100. By adding suitable interface software, the processing unit 100 can be controlled from the control panels of patient tables or X-Ray consoles made by GE, Philips, Siemens, etc.

The following summarizes features and performance characteristics of the componentized system depicted in FIG. 1, some of which have been discussed previously herein above.

Generated/Displayed Images

The system supports a combination of tomographic and sagittal views including: tomographic IVUS images, sagittal views either vertically or horizontally simultaneous with tomographic display. All measurements are displayed on imaging views. Data capture and display is carried out in the form of recorded video loops and still images. The system supports replaying and reviewing captured images, data capture and display in all modes including: virtual histology, flow. A variety of imaging technologies include Intracardiac Echocardiography (ICE), flow, pressure, etc.

With regard to the display screen, text is displayed by default in English. Additional supported languages include: French, Italian, German, and Spanish. Other displayed information includes: patient demographic information; current date, time, software version; patient co-morbidity data (in the patient screen); measurements, including distances, areas, longitudinal distances, and borders.

Catheter Support:

The processing unit 100 supports a variety of cardiovascular and peripheral IVUS catheters (both array and rotating crystal) and flexibly supports later developed catheter designs including Intracardiac Echocardiography (ICE) and capacitive Microfabricated Ultrasonic Transducer (cMUT) catheters.

Instrument Set Up/Functions:

Standard local video output is provided as well as multiple remote video outputs. Communications set up include network (DICOM) and Ethernet RJ-45. A connector on the processing unit 100 chassis supports remote USB control panel, trackball or keyboard input. The system supports communication with a remote archiving station for color image printing and DVD recording of patient data. The system supports interfacing with controls of others including GE, Siemens, Philips, etc.

Mechanical Design:

The system components all have computer components and printed circuit boards integrated into a small, reduced weight, housing, suitable for mounting on, or near the patient table in a catheter lab or alternatively a remote location within 30-50 meters of the patient (depending on the component) in a remote control or equipment room. The control panel 110 is mounted from the DIN rails on the patient table 102 in the catheter lab and/or a remote control room. The control panel 110 connects to the processing unit 100 by a single cable. The control panel 110 also includes mounting hardware for mounting from a roll around equipment cart or from a wall. The Control Panel enclosure is also attachable to a boom/arm/mount that can be mounted on or to the control area of the patient table. It should also be capable of being mounted to a roll around IV pole cart. It should also be possible to place it on a flat table for desktop use.

Display:

The monitor 112 is any of a variety of available monitors including 15/17/19 inch (diagonal) flat panel LCD monitors. The monitor is of suitable quality such that the monitor screen is visible in a reduced light catheter lab environment with minimal distortion when viewed from side or off angle (up to 40-45 degrees off angle). The display is mountable in a variety of ways including on an articulated arm that allows the display position to be changed from stowed under the patient table, to easily visible at the patient table. The display is also mountable via a bracket attached to the patient table 102.

Control Panel:

The control panel connects to the processing unit 100 via a USB cable and permits operation of the GUI and patient data entry using the pull out keyboard. The control panel is mountable on or near the patient table 102, on a freestanding mobile IV pole carrier, or from an articulated wall mounted arm, depending on user preferences. The control panel communicates with the processing unit from a remote control room User Interface:

The user interface embodied in the monitor 112 displays and the control panel 110 (described herein below) provide an intuitive, easy to use interface that follows a typical IVUS case workflow. The user can use the mechanical keys on the control panel or, after powering on, navigate via soft keys on the user interface. The primary operator control is provided through on-screen curser and screen controls on the monitor 112 display. When operating in a virtual histology mode, the system supports plaque/tissue characterization and volume determinations, including user driven border editing on the tomographic and in-line digital views, and reanalysis of statistics. A remote archiving station consolidates the tasks of saving data, printing data and/or networking data.

Data Storage:

A variety of data storage is supported by the exemplary system including the following:

Primary Storage Medium: Internal CPU hard drive(s).

Secondary Storage: Media will be DVD-R disks for archival purposes.

Tertiary Storage: Hospital DICOM server via the PACS network.

Quaternary Storage: Removable USB flash drive for transfer to a workstation.

Ability to review data on systems from both primary and secondary sources.

Ability to view Volcano images on a computer, such as in their office or home

Minimum three, 90 second video loops stored @ 30 fps

LCD/CPU Specification

In an alternative embodiment the monitor 112 and the processing unit 100 are contained within a single housing and used in hospital catheter laboratories. It is designed to mount from the patient table mounting rails using mounting hardware. The following specifications describe the design details for this variation of the above-described componentized system.

The case has overall dimensions of 15" H×17" W×5" D and a weight of approximately 25 pounds (about 10 Kg). Cooling is provided via a 1×80-120 ccm cooling fan, blowing air into case, exiting from bottom or sides. The processor is a low power, dual-core PENTIUM Sossaman processor.

The motherboard includes at least two PCI slots for connecting hosted digital and analog boards of the processing unit 100.

Figure 5:
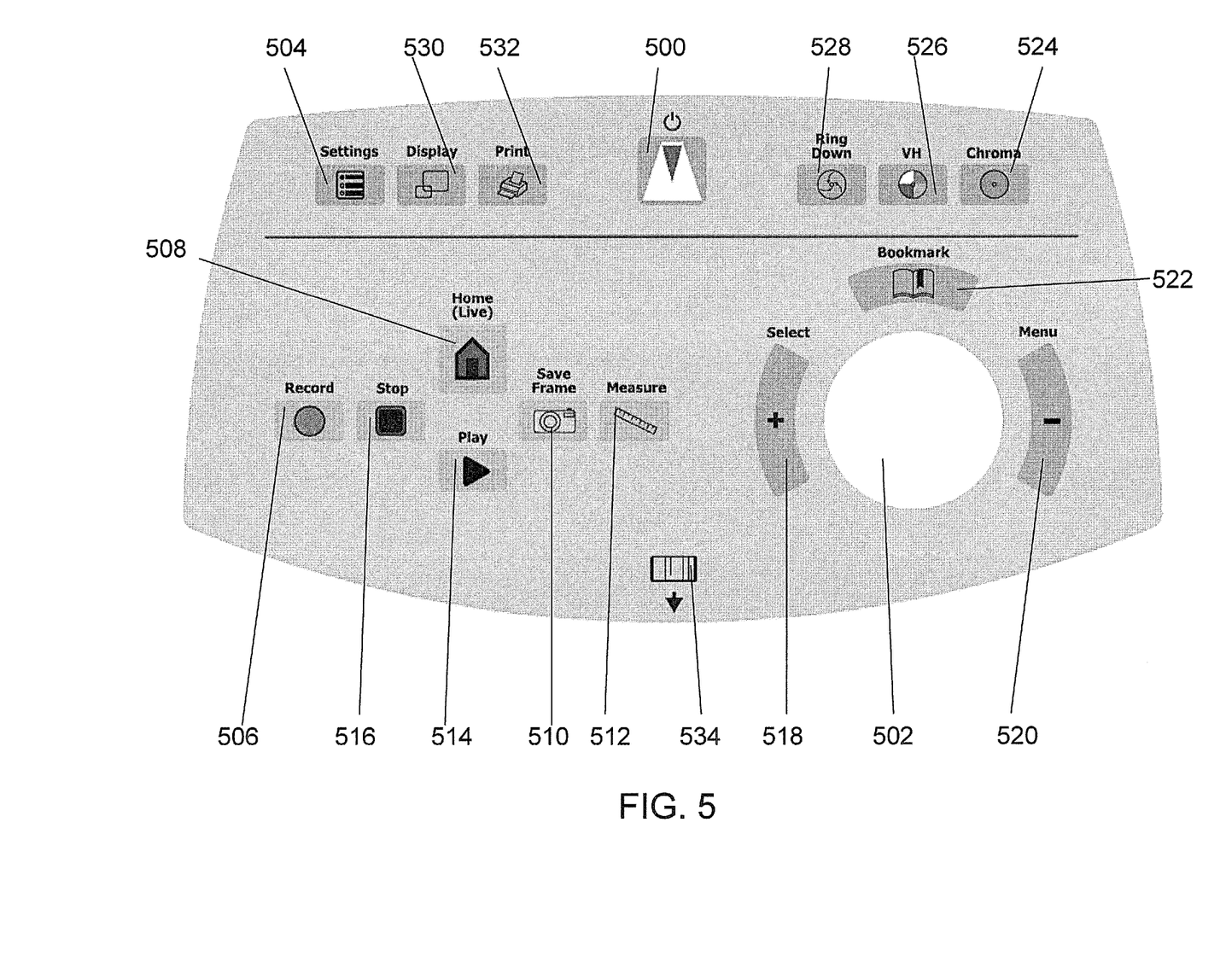
FIG. 5 illustratively depicts an exemplary control panel configuration.

Turning to FIG. 5, an exemplary control panel button/trackball interface is depicted. In general, a user interacts with the system through the control panel 110 via a set of buttons configured, by way of example in a manner set forth in FIG. 5. The elements of the control panel include: a Power on/off 500; a trackball 502 (used to position the cursor on the screen of the monitor 112); screen selection keys including Settings 504, Record 506, Home 508, Save Frame 510, measure 512, play 514, and stop 516; Select (+) 518 and Menu (−) 520 keys; a Bookmark 522 key; a standard alphanumeric keyboard (retracted below control panel); a ChromaFlo® 524 key; a VH 526 key; a ringdown key 528; a display key 530; a print key 532; and a Keyboard indicator 534. The functionality of each of these elements is discussed herein below.

In an exemplary embodiment the various action/control buttons are grouped to facilitate user workflow and include color coding coordinating with the software keys and icons to promote ease of use. A power button 500 turns the system on or off and illuminates when the system is plugged in. In addition to the power button 500, a set of buttons along a top row (e.g., settings 504, display 530, and print 532) facilitate set-up and mode selection. These top-row buttons/actions are generally not part of the routine work flow. The two groups include:

Set-up & Display
 Settings 504: Changes system settings like date and time; also permits setting and editing default configurations.
 Display 530: Displays a large IVUS image with measurements and demographics to facilitate large viewing.
 Print 532: Prints a 6×4 inch photo of the current image on the screen
Modes
 Ringdown 528: Turn Ring Down on or off
 VH Mode 526: Turns virtual histology display on or off
 ChromaFlo (flow image) 524: Turns ChromaFlo on or off
 Two groups of buttons/controls lie below the top row. The two groups are action-oriented and designed with the user in mind to facilitate ease of use and retention of training. These buttons are typically used during a routine patient case:
Workflow Buttons that Facilitate Ease of Use of System
 Record 506: Records a video loop
 Stop 516: Stops the recording of a video loop. Press to Freeze a live image
 Home 508: Press to view the live image
 Play 514: Play a recorded video loop
 Save Frame 510: Press during Live mode to save one frame
 Measure 512: Provides access to measurement options such as diameter, length and borders
Buttons Grouped around the Trackball to Facilitate Navigation during the Patient Case
 Select (+) 518: Press to select tabs, areas, or points. It is similar to left-clicking with a mouse.
 Menu (−) 520: Press to end your selection points. It is similar to right-clicking with a mouse.
 Bookmark 522: Press while recording a loop to select specific areas of interest
Trackball 502
 The trackball 502 moves the cursor on the monitor 112 to allow function selection. The trackball 502 is also useful for selecting annotation locations and making measurements.
 Keyboard 534: Points to the retractable keyboard beneath the control panel
Alphanumeric Keyboard
 A standard alphanumeric keyboard is contained in a retracting tray under the control panel button/user interface and is used for data entry and image annotation. To use the keyboard, pull the latch underneath the keyboard tray and pull the keyboard tray out.

Figure 6:
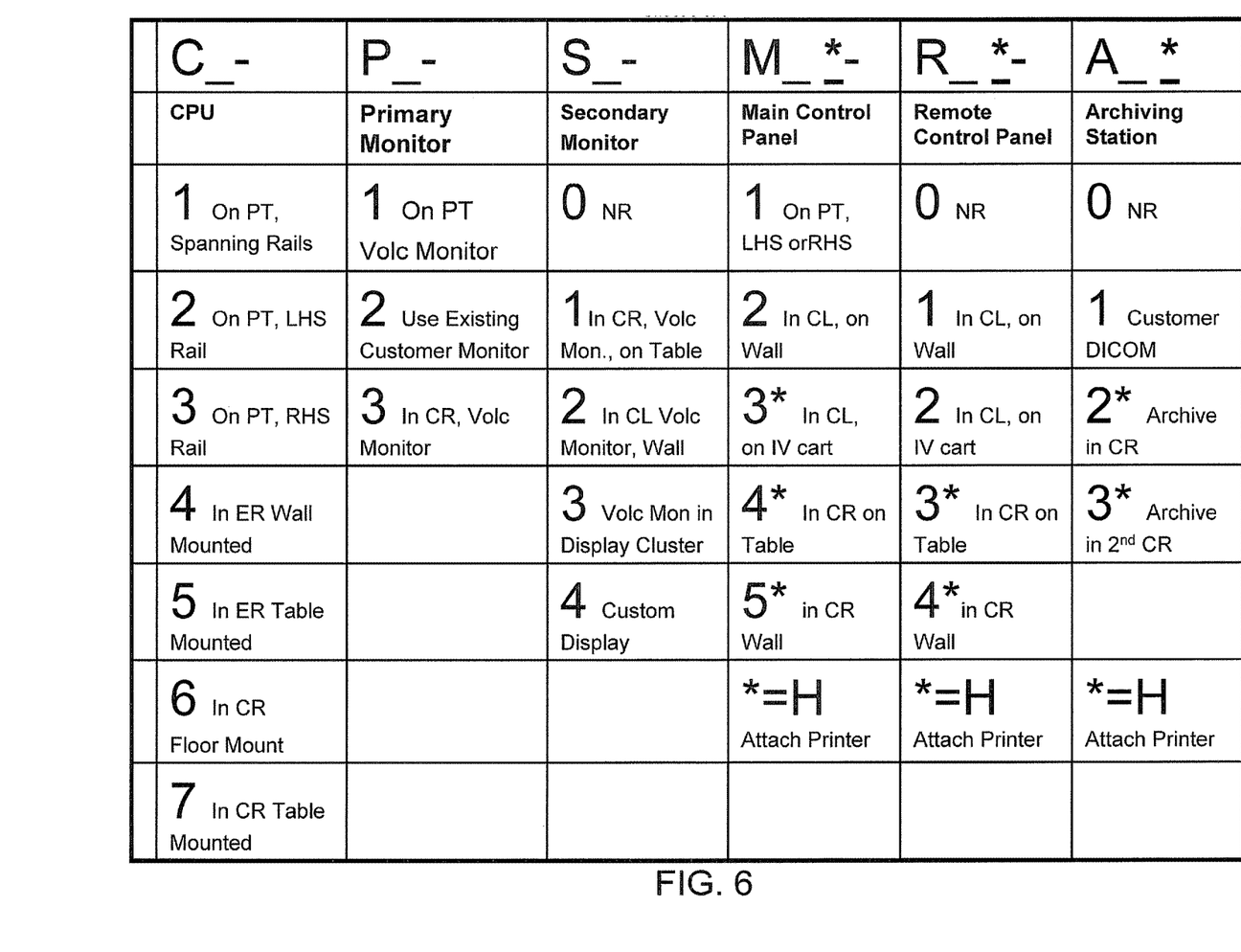
FIG. 6 comprises a chart outlining a variety of configuration options supported by an exemplary componentized system.

Turning briefly to FIG. 6, a two dimensional array presents a set of options associated with each of a set of components that make up the system. The extent of the choices for each component demonstrates the high degree of configurability and adaptability of the system to various users' needs. The following options are available for the processing unit 100 (that includes a DVD burner/player for archiving and retrieval), location:
 1—CPU on patient table, spanning rails
 2—CPU on patient table LHS, rail mounted
 3—CPU on patient table RHS, rail mounted
 4—CPU in Equipment Room, wall mounted
 5—CPU in Equipment Room, table mounted
 6—CPU in Control Room, floor standing
 7—CPU in Control Room, wall mounted
The following options are available for Primary Monitor location:
 1—Volcano LCD Monitor, Pt table "foot end" mounted, arm attached to rail
 2—Use existing monitor in display cluster (Determine if XGA compatible and where aux video input is located)
 3—Remote display, on table in Control Room (Determine cable length from CPU, if >15 ft, use Ethernet link and I/O box)
The following options are available for Secondary Monitor location:
 0—None required
 1—Remote Volcano display, located on table top in Control Room
 2—Wall mounted Volcano display located in Cath Lab
 3—Volcano display added to display cluster
 4—Existing display, mounted in display cluster (Determine if XGA compatible and if switched video input is available)
The following options are available for Main Control Panel location:
 1—Attached to pt table rail, LHS, or RHS
 2—Attached to wall mount in Cath Lab
 3—Attached to IV portable cart in Cath Lab
 4—In Control Room, table mounted
 5—In Control Room, wall mounted
 H—For 3, 4, 5 above, attach color printer
The following options are available for Remote Control Panel location:
 0—None required
 1—Attached to wall mount in Cath Lab
 2—Attached to IV portable cart in Cath Lab
 3—In Control Room, table mounted
 4—In Control Room, wall mounted
 H—For 3, 4 above, attach color printer
The following options are available for Archiving Station:
 0—None required
 1—Use DICOM workstation for archive 2—Volcano Archive station in Control Room
3—Volcano Archive station in Second Control Room
H—For 2, 3 above, attach color printer The above described component option sets are exemplary and are by no means limiting in nature as the disclosed system is designed with the intention of supporting a highly configurable system.

Systems and their associated components have been described herein above with reference to exemplary embodiments of the invention including their structures and techniques. In view of the many possible embodiments to which the principles of this invention may be applied, it should be recognized that the embodiments described herein with respect to the drawing figures are meant to be illustrative only and should not be taken as limiting the scope of invention. Therefore, the invention as described herein contemplates all such embodiments as may come within the scope of the following claims and equivalents thereof.

What is claimed is:

1. A componentized system for acquisition and display of intravascular information, comprising:
   a patient interface module (PIM) adapted to be coupled to an intravascular imaging catheter and configured to receive intravascular ultrasound (IVUS) data for generating IVUS images of a vessel during a catheter-based imaging operation in a catheterization lab;
   a monitor configured to display the IVUS images of the vessel;
   a first control panel positioned within the catheterization lab and adapted to control acquisition of the IVUS data using the intravascular imaging catheter, display of the IVUS images, and a first measurement of anatomy shown in the IVUS images;
   a second control panel positioned in a control room remote from the first control panel and adapted to control the display of the IVUS images and a second measurement of anatomy shown in the IVUS images; and
   a processing unit, communicatively coupled to the PIM, the first control panel, the second control panel, and the monitor, the processing unit adapted to generate the IVUS images from the IVUS data received by the PIM,
   wherein the PIM, the first control panel, the second control panel, and the monitor are independently with regard to one another,
   wherein the first and second control panels are simultaneously active to transmit commands to the processing unit during the acquisition of the IVUS data, the display of the IVUS images, and the first and second measurements of the anatomy shown in the IVUS images,
   wherein the first and second control panels are adapted to independently control the display of the IVUS images and the first and second measurements of the anatomy shown in the IVUS images, and
   wherein the processing unit is adapted to receive and process the commands such that the first and second control panels are adapted to transmit the commands to the processing unit without locking out the other.

2. The componentized system of claim 1 wherein communications interfaces and physical cabling support communications between the PIM and the processing unit in instances where the processing unit is located outside a region proximate a patient table.

3. The componentized system of claim 2 wherein a communications link between the PIM and the processing unit includes a buffer amplifier.

4. The componentized system of claim 1 wherein a communications link between the processing unit and the monitor extends beyond a region proximate a patient table.

5. The componentized system of claim 4 wherein the communications link includes a buffer amplifier.

6. The componentized system of claim 1 wherein the processing unit is further adapted to support archiving patient data including images generated by the processing unit.

7. The componentized system of claim 1 wherein the second control panel comprises a third party control panel provided by a catheter lab control station distinct from the componentized system.

8. The componentized system of claim 1 wherein at least one of the monitor, the first control panel, the second control panel, or the processing unit are flexibly integrated with catheter lab infrastructure through a set of connection brackets.

9. The componentized system of claim 8 further comprising a set of integration configuration options characterizing a manner in which at least one of the monitor, the first control panel, the second control panel, or the processing unit are integrated with the catheter lab infrastructure.

10. The componentized system of claim 1 wherein the first control panel comprises a set of controls arranged into a set of regions based upon their workflow roles.

11. The componentized system of claim 10 wherein the regions comprise: a setup region including a set of buttons facilitating setup of the system prior to acquiring patient images.

12. The componentized system of claim 11 wherein the setup region is positioned at a portion of the control panel distal to a user of the first control panel.

13. The componentized system of claim 10 wherein the regions comprise: an action-oriented region including a set of buttons accessed while acquiring images from a patient.

14. The componentized system of claim 13 wherein the action-oriented region is positioned at a portion of the first control panel proximal to a user of the first control panel.

15. An intravascular imaging system, comprising:
   a first control panel positioned in a catheterization lab proximate to a patient during a catheter-based imaging operation, wherein the first control panel includes a first plurality of input options to control acquisition of intravascular ultrasound (IVUS) image information by an intravascular imaging catheter positioned within a vessel of the patient, display of display of IVUS images, and a first measurement of anatomy shown in the IVUS images;
   a second control panel positioned in a control room remote from the first control panel, the second control panel including a second plurality of input options to control display of the IVUS images and a second measurement of the anatomy shown in the IVUS images; and
   a processing unit in communication with the first and second control panels, the processing unit operable to process commands from the first and second control panels such that the first and second control panels are simultaneously able to control aspects of the imaging operation including the display of the IVUS images, and the first and second measurements of the anatomy shown in the IVUS images,
   wherein the processing unit is adapted to receive and process the commands such that the first and second control panels transmit the commands to the processing unit without locking out the other.

16. The intravascular imaging system of claim 15 wherein the first control panel includes controls for selecting modes of IVUS operation.

17. The intravascular imaging system of claim 15 wherein the first control panel includes pointer navigation controls supporting multi-button mouse functionality.

18. The componentized system of claim 1, wherein:
the first control panel includes a first plurality of input options, the first plurality of input options comprising subsets of input options respectively associated with the acquisition of IVUS data using the intravascular imaging catheter, the display of IVUS images, and the first measurement of anatomy shown in the IVUS images; and
the second control panel includes a second plurality of input options, the second plurality of input options comprising subsets of input options respectively associated with the display of IVUS images and the second measurement of anatomy shown in the IVUS images.

19. The intravascular imaging system of claim 15, wherein the first and second control panels are simultaneously active to transmit commands to the processing unit during acquisition of the IVUS image information, the display of the IVUS images, and the first and second measurements of anatomy shown in the IVUS images.

20. The intravascular imaging system of claim 15, wherein the first and second control panels are adapted to independently control the display of the IVUS images, including the display of two or more images based on IVUS data.

21. The intravascular imaging system of claim 15, wherein the display of two or more images based on IVUS data comprise different views of a same region of the anatomy.

22. The intravascular imaging system of claim 15, wherein the first and second control panels are adapted to send asynchronously processed control instructions to the processing unit.

23. The intravascular imaging system of claim 15, wherein the second control panel includes pointer navigation controls supporting multi-button mouse functionality.

24. The componentized system of claim 1, wherein the first control panel comprises a first touch interface adapted to control the display of the IVUS images and measurements of anatomy shown in the IVUS images.

25. The componentized system of claim 24, wherein the second control panel comprises a second touch interface adapted to control the display of the IVUS images and measurements of anatomy shown in the IVUS images.

26. The componentized system of claim 1, wherein the first and second control panels are adapted to receive commands from one or more users, wherein the first and second control panels are adapted to send asynchronously processed control instructions to the processing unit based on the received commands.

* * * * *